United States Patent
Nott et al.

(10) Patent No.: US 6,273,900 B1
(45) Date of Patent: Aug. 14, 2001

(54) BLOOD CLOT FILTERING

(75) Inventors: Sepideh H. Nott, Canton; Hannah S. Kim, Boxborough; Naroun Soun, Lynn; David L. Sandock, Littleton, all of MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

(21) Appl. No.: 09/008,258

(22) Filed: Jan. 16, 1998

Related U.S. Application Data (63) Continuation of application No. 08/346,733, filed on Nov. 30, 1994, now Pat. No. 5,709,704.

(51) Int. Cl.$^7$ .................................................. A61M 29/00
(52) U.S. Cl. ............................................. 606/200; 606/159
(58) Field of Search ..................................... 606/200, 127, 606/113, 110, 158, 159, 198; 128/312, 319, 897, 898, 894

(56) References Cited

U.S. PATENT DOCUMENTS

| | | |
|---|---|---|
| 3,540,431 | 11/1970 | Mobin-Uddin et al. . |
| 3,952,747 | 4/1976 | Kimmell, Jr. . |

(List continued on next page.)

FOREIGN PATENT DOCUMENTS

| | | |
|---|---|---|
| 3417738 | 11/1985 | (DE) . |
| 40 30 998 A1 | 4/1991 | (DE) . |
| 0 348 295 A1 | 12/1989 | (EP) . |
| 0 430 848 A1 | 5/1991 | (EP) . |
| 0 437 121 A2 | 7/1991 | (EP) . |
| 0 462 008 A1 | 12/1991 | (EP) . |
| 0 472 334 A1 | 2/1992 | (EP) . |
| 8909642 | 7/1989 | (FR) . |
| 2 649 884 | 1/1991 | (FR) . |
| 2649884 * | 4/1995 | (FR) ..................................... 606/200 |
| 2 200 848 A | 8/1988 | (GB) . |
| 2 200 848 B | 2/1991 | (GB) . |
| 835447 | 5/1979 | (RU) . |
| 1103868 A | 7/1983 | (RU) . |
| 955912 A | 2/1988 | (RU) . |
| WO 91/04716 | 4/1991 | (WO) . |
| WO 91/11972 | 8/1991 | (WO) . |
| WO 95/09567 * | 4/1995 | (WO) ..................................... 606/200 |

OTHER PUBLICATIONS

Kraimps et al., "Conical Endocaval Filters with Metallic Struts: Search for a New Model", 3/92, Ann. Vasc. Surg., 6:99–110.

Kraimps et al., "Optimal Central Trapping (OPCETRA) Vena Caval Filter: Results of Experimental Studies", 11/92, J. of Vasc. and Inter. Rad., 3:697–701.

Primary Examiner—Henry J. Recla
Assistant Examiner—Lien Ngo
(74) Attorney, Agent, or Firm—Hoffman & Baron, LLP (57) ABSTRACT

A blood clot filter comprising: an anchoring portion comprising a generally cylindrical self-expanding body formed from resilient material, the generally cylindrical body having proximal and distal ends and defining an axial direction and having a structure of variable size diameter expandable from a low-profile compressed condition to a larger profile expanded condition, wherein the resilient material urges the generally cylindrical body to radially expand and to thereby apply anchoring radial force against the inner wall surface of the blood vessel; and a generally conical filtering portion axially aligned with the generally cylindrical body having an open proximal end coupled to the distal end of the anchoring portion and having an apical distal end. Also disclosed is a blood clot filter having one or more hooks fixedly coupled to the anchoring portion and formed from compliant material having an original shape that bends under stress yet returns to its original shape when unstressed. The hooks respectively tend to project from the anchoring portion at an acute angle with respect to the axial direction for engagement with a vessel wall. Also, the hooks are deflectable toward the anchoring portion for achieving a low-profile.

41 Claims, 6 Drawing Sheets

U.S. PATENT DOCUMENTS

| | | |
|---|---|---|
| 4,425,908 * | 1/1984 | Simon .................................. 606/200 |
| 4,494,531 * | 1/1985 | Gianturco .......................... 128/1 R |
| 4,619,246 * | 10/1986 | Molgaard-Nielsen et al. .......... 128/1 |
| 4,643,184 | 2/1987 | Mobin-Uddin . |
| 4,655,771 | 4/1987 | Wallsten . |
| 4,688,553 | 8/1987 | Metals . |
| 4,727,873 * | 3/1988 | Mobin-Uddin ...................... 606/200 |
| 4,781,177 | 11/1988 | Lebigot . |
| 4,793,348 | 12/1988 | Palmaz . |
| 4,817,600 | 4/1989 | Herms et al. . |
| 4,830,003 | 5/1989 | Wolff et al. . |
| 4,832,055 | 5/1989 | Palestrant . |
| 4,856,516 | 8/1989 | Hillstead ............................. 128/343 |
| 4,873,978 | 10/1989 | Ginsburg . |
| 4,943,297 * | 7/1990 | Saveliev .............................. 606/200 |
| 4,954,126 | 9/1990 | Wallsten . |
| 4,957,501 | 9/1990 | Lahille et al. . |
| 4,969,891 | 11/1990 | Gewertz . |
| 4,990,156 * | 2/1991 | Lefebvre ............................ 606/200 |
| 5,059,205 | 10/1991 | El-Nounou et al. . |
| 5,061,275 | 10/1991 | Wallsten et al. . |
| 5,071,407 | 12/1991 | Termin et al. . |
| 5,108,418 * | 4/1992 | Lefebvre ............................. 606/200 |
| 5,108,419 | 4/1992 | Reger et al. . |
| 5,133,733 | 7/1992 | Rasmussen et al. . |
| 5,135,516 | 8/1992 | Sahatjian et al. . |
| 5,152,777 | 10/1992 | Goldberg et al. . |
| 5,160,342 * | 11/1992 | Reger et al. ......................... 606/200 |
| 5,190,546 | 3/1993 | Jervis . |
| 5,221,261 | 6/1993 | Termin et al. . |
| 5,224,953 | 7/1993 | Morgentaler . |
| 5,300,086 | 4/1994 | Gory et al. . |
| 5,304,121 | 4/1994 | Sahatjian . |
| 5,304,200 | 4/1994 | Spaulding . |
| 5,324,304 | 6/1994 | Rasmussen . |
| 5,329,942 | 7/1994 | Gunther et al. . |
| 5,344,427 * | 9/1994 | Cottenceau et al. ................. 606/200 |
| 5,370,657 | 12/1994 | Irie . |
| 5,375,612 | 12/1994 | Cottenceau et al. . |
| 5,382,261 | 1/1995 | Palmaz . |
| 5,405,377 | 4/1995 | Cragg ....................................... 623/1 |
| 5,476,508 | 12/1995 | Amstrup ................................... 623/1 |
| 5,709,704 * | 1/1998 | Nott et al. ............................ 606/200 |

\* cited by examiner

BLOOD CLOT FILTERING

This is a continuation of U.S. application Ser. No. 08/346,733, filed Nov. 30, 1994, now U.S. Pat. No. 5,709,704.

FIELD OF THE INVENTION

This invention relates to blood clot filtering.

BACKGROUND

Blood clots that form in the lower part of the body may migrate to the heart and may be subsequently pumped to the lungs. Small clots can be absorbed by the body without adverse effect. However, larger clots can interfere with the oxygenation of blood (e.g., on the order of 3 mm in diameter and 10–30 cm in length) and can possibly cause shock or sudden death.

Many transvenous filtering devices have been developed for installation in the vena cava to prevent especially large clots from reaching the lungs. These filters have fine wires positioned in the blood flow to catch and hold clots for effective lysing in the blood stream. Some of these devices are inserted into the vena cava by dissecting the internal jugular vein in the neck or the femoral vein in the groin, inserting a metallic capsule containing a filtering device to the proper position in the vena cava, and releasing the filtering device into the vena cava. More recently, filters have been designed for percutaneous introduction into the vasculature.

SUMMARY

In one aspect, the invention features a filter sized and constructed to be compressed and passed through the vasculature of a patient to be anchored against an inner wall surface of a blood vessel for capturing blood clots in a blood stream passing therethrough. The filter comprises: an anchoring portion comprising a generally cylindrical self-expanding body formed from resilient material, the generally cylindrical body having proximal and distal ends and defining an axial direction and having a structure of variable size diameter expandable from a low-profile compressed condition to a larger profile expanded condition, wherein the resilient material urges the generally cylindrical body to radially expand and to thereby apply anchoring radial force against the inner wall surface of the blood vessel; and a generally conical filtering portion axially aligned with the generally cylindrical body having an open proximal end coupled to the distal end of the anchoring portion and having an apical distal end, the anchoring portion and the filtering portion being substantially non-overlapping to achieve a low profile compressed condition for delivery of the filter through the vasculature.

Embodiments of the invention may include one or more of the following features. The generally conical filtering portion is preferably formed from a plurality of elongated strands arranged to form a generally conical structure to guide blood clots in the blood stream flowing there past to the apical distal end of the generally conical filtering portion for lysing. The elongated strands forming the generally conical filtering portion are preferably constructed and arranged to maintain a generally conical shape whether the anchoring portion is in a compressed condition or an expanded condition. The anchoring portion and the filtering portion are preferably constructed and arranged so that the proximal end of the filtering portion conforms to the shape of the cylindrical body of the anchoring portion. The elongated strands are preferably fixedly attached to one another only at the apex of the generally conical filtering portion. The elongated strands may be formed from nitinol (nickel-titanium alloy), plastically deformable material, temperature-sensitive shape memory material with a transition temperature around body temperature, or elastic material having a core formed from radiopaque material. The filter may be coated with a drug for in vivo compatibility. The resilient elongated strands preferably extend from the proximal end of the anchoring portion to the distal apical end of the filtering portion.

The elongated strands of the filtering portion may define a plurality of neighboring filtering cells. The neighboring filtering cells are preferably loosely coupled together at the respective areas of contact between neighboring cells. The neighboring cells are preferably coupled together by helical twisting of portions of respective elongated strands of neighboring cells. The portion of the twisted-together elongated strands are preferably capable of slight mutual separation to accommodate changes in the shapes of the cells from the expanded to the compressed conditions. The generally conical filtering portion preferably comprises at least two rings of cells, wherein the cells of each ring are of substantially equal size and are spaced substantially the same distance from the apical distal end of the filtering portion. The size of the cells in the rings is preferably smaller for cells closer to the apical distal end of the filtering portion than for cells located a greater distance from the apical distal end of the filtering portion.

The elongated strands of the filtering portion may be spirally arranged with respect to one another from the proximal end of the filtering portion to the apical distal end of the filtering portion. The elongated strands are preferably selected to have sufficient rigidity to maintain the generally conical shape of the filtering portion.

The self-expanding anchoring portion preferably comprises a ring of neighboring cells. The cells of the anchoring portion are preferably self-expanding. The cells of the anchoring portion preferably cooperate to urge the generally cylindrical body of the anchoring portion to radially expand from a compressed condition to an expanded condition. The neighboring cells of the anchoring portion are preferably fixedly coupled together at respective areas of contact. The cells of the anchoring portion are preferably formed from one or more resilient elongated strands. When the generally cylindrical body is in a compressed condition, the cells of the anchoring portion are preferably elongated in the axial direction.

In another general aspect, the invention features a blood clot filter comprising: an anchoring portion formed from resilient material having proximal and distal ends and having a generally circular transverse cross-section defining an axial direction, the anchoring portion further having a structure of variable size diameter expandable from a low-profile compressed condition to a larger profile expanded condition, wherein the resilient material urges the anchoring portion to radially expand and to thereby apply anchoring radial force against the inner wall surface of the blood vessel; a filtering portion axially aligned with the generally cylindrical body having an open proximal end coupled to the distal end of the anchoring portion; and one or more hooks fixedly coupled to the anchoring portion formed from compliant material having an original shape that bends under stress yet returns to its original shape when unstressed, said one or more hooks respectively tending to project from the anchoring portion at an acute angle with respect to the axial direction for engagement with a vessel wall, the one or more hooks further being deflectable toward the anchoring portion for achieving a low-profile.

Embodiments of the invention may include one or more of the following features. The hooks are preferably formed from nitinol. The hooks preferably preferentially bend toward and away from the vessel wall engaging portion. The hooks are preferably formed from flat nitinol wire having a width dimension and having a thickness dimension substantially smaller than the width dimension for achieving preferential bending; the flat nitinol wire being oriented so that the thickness dimension of the flat nitinol wire coincides with a radial direction of the anchoring portion. The hooks preferably preferentially bend toward and away from the vessel wall engaging portion.

Among the advantages of the present invention are the following. Because the anchoring portion and the filtering portion have constructions that are optimally designed for their respective functions, the filter can have a low profile while providing a robust design that can readily accommodate different vessel sizes. Furthermore, the anchoring portion serves to center the filtering portion. The filtering portion of the filter should have a small enough capture cross-section to prevent large clots from passing therethrough. This requires a sufficient amount of filtering material (e.g., elongated strands) to reduce the capture cross-section. Since the conical filtering portion according to the present invention does not also have to support the filter in the vessel, smaller-sized elements can be used to form the filter to achieve a lower profile. The profile of the present invention can be made small, while providing substantially the same anchoring force and substantially the same filtering efficiency as, e.g., a GREENFIELD® 24 Fr stainless steel filter (available from Medi-Tech, Inc. of Watertown, Mass., U.S.A.). The filter designs minimally disturb blood flow, while achieving a desirable level of filtering efficiency. Since the sizes of the cells of the filtering portion decrease from the proximal end to the distal end, larger cells are positioned near the vessel walls where the flow velocity is relatively low and smaller cells are positioned in the central region of the vessel where the flow velocity is highest and where the most effective clot lysing occurs. Without being limited to a particular theory, it is believed that clots traveling with lower velocity do not pass through the larger size cells in the periphery of the conical filtering portion, but are instead guided to the apical distal end of the filtering portion. Clots traveling with higher velocities in the central region of the vessel, which may otherwise pass through the larger size peripheral cells, are caught in the smaller size cells located at the distal end of the filtering portion. Because the radial force against the vessel wall is distributed along a length of the vessel wall a filter according to the present invention offers higher resistance to migration as well as less trauma to the vessel wall.

Other features and advantages will become apparent from the following description and from the claims. For example, the invention features a process for making a blood clot filter and a method for treating a patient by implanting a blood clot filter into a blood vessel of the patient.

DESCRIPTION

STRUCTURE

Referring generally to FIGS. 1–1C and 2–2B, a blood clot filter 10 includes a generally cylindrical anchoring portion 12 and a generally conical filtering portion 14 terminating at a closed, distal apical end 16. The cylindrical portion uniformly exerts an outward radial force to anchor the filter in a blood vessel (e.g., the vena cava) in which it is disposed; the exerted force being sufficient to prevent migration of the filter in the vessel. The generally cylindrical shape of the anchoring portion conforms to the inner wall surface of a blood vessel and properly centers the filtering portion within the vessel. The filtering portion provides a conical meshwork across the blood vessel to catch and retain clots in the blood stream.

Figure 1:
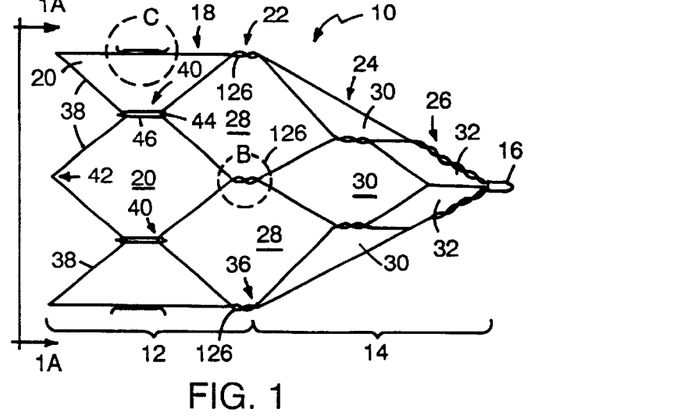
FIGS. 1 and 1A are diagrammatic side and end views of a filter in an expanded condition.
Figure 1A:
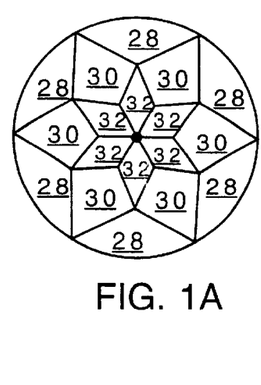
Figure 2:
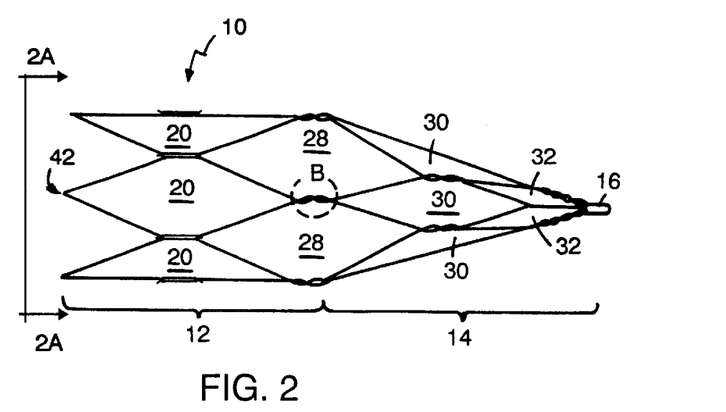
FIGS. 2 and 2A are diagrammatic side and end views of a filter in a compressed condition.
Figure 2A:
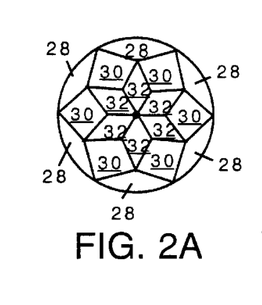

Cylindrical portion 12 is formed by a ring 18 of circumferentially arranged cells 20. Filtering portion 14 is formed by a series of three rings (22, 24, 26) of relatively loosely connected cells (28, 30, 32, respectively). The size of the cells forming the rings of the filtering portion increases from apical end 16 of the filtering portion to the proximal end 34 of the filtering portion, which is adjacent the distal end 36 of the anchoring portion.

Figure 1B:
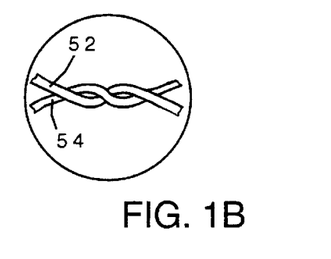
FIGS. 1B and 1C are enlarged views of respective portions of the filter shown in FIG. 1.
Figure 1C:
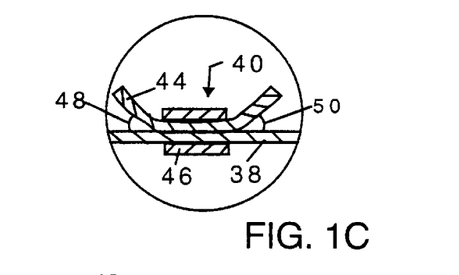

Cells 20 of the cylindrical portion of the filter are defined by elongated strands 38 of resilient material (e.g., nitinol wire). Neighboring cells are fixedly joined together at respective regions of contact 40, e.g., by spot welding, as described in detail below. Fixed regions of contact 40 enable cells 20 in ring 18 to cooperate to urge the anchoring portion into an expanded condition (FIGS. 1–1B). The fixed regions of contact 40 also prevent the elongated strands forming cells 20 from rotating about each other, which might cause hinging and locking between the cells in a manner distorting the cylindrical shape of the anchoring portion. In a compressed condition (FIGS. 2–2B) the longitudinal length of cylindrical anchoring portion 12 increases.

Conical filtering portion 14 is constructed from a series of rings (22, 24, 26) of relatively loosely coupled cells in a manner preserving its generally conical shape, whether the filter is in a compressed condition or an expanded condition.

The filtering portion does not need to provide anchoring radial force. However, the material substance forming the conical structure has sufficient structural integrity to prevent large clots in the blood flow from displacing the filtering structure. The size of the cells in the filtering portion are selected to minimally disturb the blood flow (which would otherwise encourage occlusion of the vessel), while still achieving a desired level of blood clot filtering.

In the embodiment shown in FIGS. 1–1C and 2–2B, the cells forming the filtering portion are coupled together by helically twisting together respective portions of the elongated strands defining neighboring cells. This coupling permits some rotation about the joints in a manner that preserves the generally conical shape of the filtering portion, whether the filter is in a compressed condition or an expanded condition.

Figure 2B:
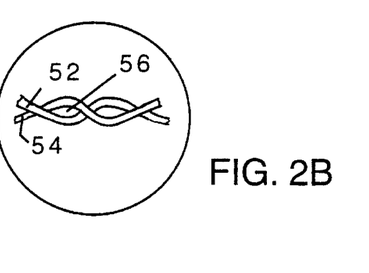
FIG. 2B is an enlarged view of a portion of the filter of FIG. 2.

Comparing FIGS. 1B and 2B, in the expanded condition (FIG. 1B), the twisted wire portions 52, 54, coupling neighboring cells in the filtering portion of the filter, are tightly wrapped about each other. However, in a compressed condition (FIG. 2B), wire portions 52, 54 move away from (and rotate about) one another to form gaps 56. This rotation or hinging prevents the build-up of internal forces within the filtering portion, which could cause the filtering portion to bow outward into a hemispherical shape, which would result in less effective blood clot filtering.

Referring back to FIG. 1C, a hook 44 formed from a section of flat nitinol wire is disposed within a tube 46 (e.g., a hypotube) and mounted at regions of contact 40 between neighboring cells in ring 18, which forms the cylindrical portion of the filter. A central region of hook 44 is mounted at regions of contact 40. Hook 44 is bent at its proximal and distal ends to respectively form acute angles 48, 50 with respect to the longitudinal axis of the cylindrical portion. The bent ends of hook 44 are oriented in divergent direction to prevent migration of the filter in proximal and distal directions. The nitinol hooks easily bend to conform to the shape of the cylindrical surface of the anchoring portion to achieve a low profile for delivery of the filter. When the filter is released into a blood vessel, the hooks return to their bent shape for engaging an inner wall surface of the vessel. Fewer hooks may be used (e.g., three hooks symmetrically disposed about anchoring portion 12 may be used) to achieve a lower profile for delivery of the filter.

In a presently preferred embodiment designed for filtering blood clots in a vena cava of about 28 mm diameter, cylindrical portion 12 includes six cells formed from nitinol wire of 0.002–0.01 inch diameter, and preferably 0.008 inch diameter (e.g., nitinol with an $A_f$ between –10° C. and +5° C. and constructed so that after drawing the wire has a tensile strength of about 250,000 psi to 300,000 psi, available from Shape Memory Applications of Sunnyvale, Calif., U.S.A.). Each cell in the anchoring portion has four side portions about 13 mm in length. Filter 10 is collapsible to a diameter of 0.08 inch (about 6 Fr). The anchoring portion has an expanded outer diameter of 30–31 mm. The filtering portion includes three rings of cells of decreasing size from the proximal end 34 to the distal apical end 16. Each of the proximalmost cells in the filtering portion has four side portions: two proximal side portions about 13 mm in length and two distal side portions about 15 mm in length. Each of the intermediate cells in the filtering portion has four side portions: two proximal side portions about 15 mm in length and two distal side portions about 11 mm in length. Each of the distalmost cells of the filtering portion has four sides portions: two proximal side portions about 11 mm in length and two distal side portions about 9 mm in length. The total length of the filter in the expanded condition is about 60 mm, with the filtering portion being about 32–34 mm in length and the anchoring portion being about 26–28 mm in length. Six hooks 44 are symmetrically disposed about the anchoring portion at each of the fixed regions of contact 40. Hooks 44 are made from flat nitinol wire about 5 mm in length, about 0.5 mm in width and about 0.05–0.15 mm thick.

Figure 3:
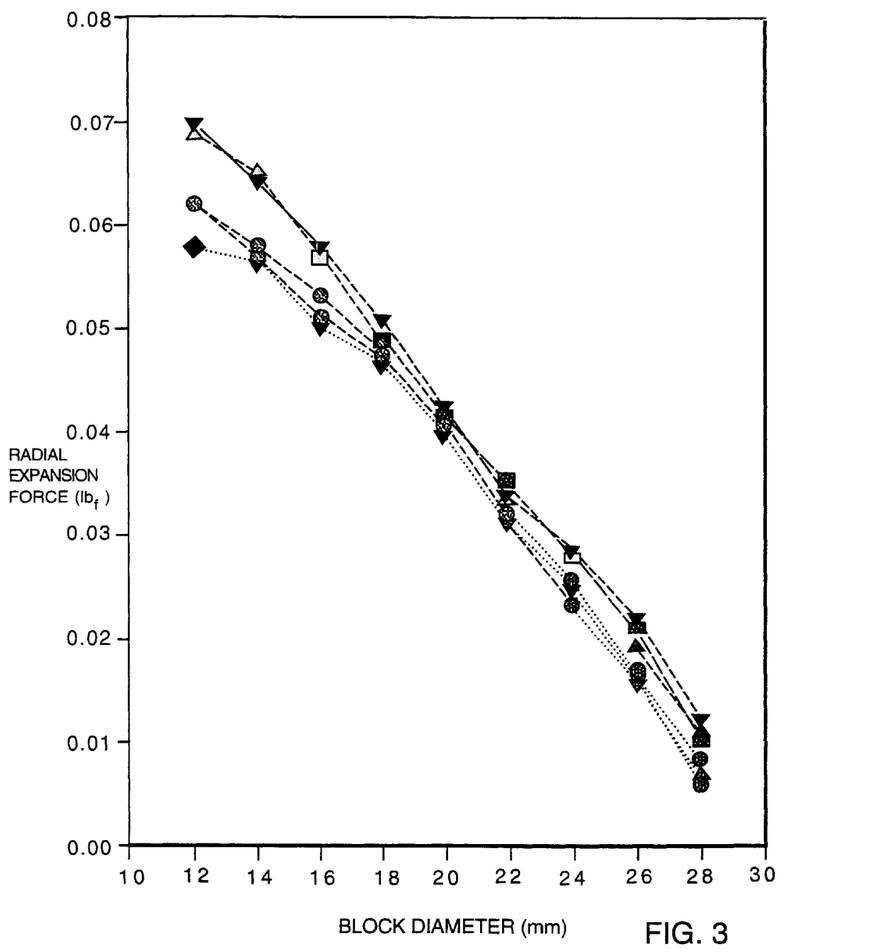
FIG. 3 is a plot of radial expansion force provided by a filter as a function of the outer diameter of the filter.

Referring to FIG. 3, the outward radial expansion forces respectively exerted by six different filters of the type shown in FIGS. 1–1C and 2–2B are plotted as a function of the outer diameter of cylindrical portion 12. The measured filters were designed with the specifications recited above. The exerted force generally varies linearly with the diameter of the anchoring portion, with the highest forces being exerted when the filter is in the lower profile conditions (i.e., most compressed). Force levels of 0.01–0.07 pounds are generally acceptable for a typical vena cava of 12–28 mm diameter. Much higher force levels may cause the filter to undesirably distort the shape of the vena cava. Also, much lower force levels would not securely anchor the filter in the vena cava and the filter may be displaced.

The number of cells in the anchoring portion and in the filtering portion may be varied to achieve larger sizes or higher forces. For example, to accommodate a so-called "mega-cava" having a diameter of up to 40 mm, the expanded outer diameter of the filter should be selected to be about 42–44 mm and the number of cells in the anchoring portion should be appropriately increased (e.g., nine cells could be used) to achieve proper outward radial force exertion to anchor the filter in the vena cava without migrating or traumatizing the vessel. Instead of increasing the number of cells, the thickness of the wire used to form the cells could be suitably increased to provide the proper amount of anchoring force. Alternatively, the exerted radial force may be increased by providing additional welds at the distal end 36 (FIG. 1) of the anchoring portion at locations 126. This increases the structural integrity of each cell 20, providing higher spring force under compression. The exerted radial force may alternatively be increased by changing the wire alloy or the degree of cold work.

Figure 3A:
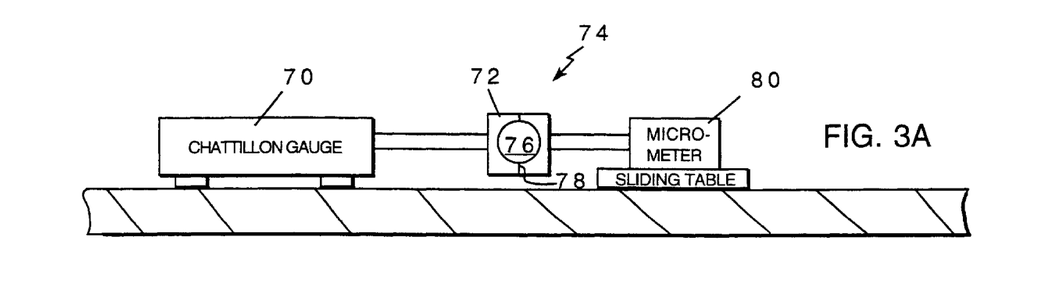
FIG. 3A is a diagrammatic side view of a system for measuring the radial force exerted by a filter as a function of the outer diameter of the filter.

Referring to FIG. 3A, the outward radial force exerted by a filter was measured using a force gauge 70 (e.g., a Chattillon gauge) attached to one half 72 of a solid block 74 through which cylindrical hole 76 of a preselected diameter is disposed. Block 74 was cut in half through a plane containing the longitudinal axis of cylindrical hole 76. A filter to be measured was placed in hole 76. A micrometer 80 attached to the other half 82 of block 74 was used to close the gap between the two halves of block 74. The force exerted by the filter was measured as a function of filter diameter by performing the measurement with a series of blocks with different preselected diameters.

Manufacture

Figure 4:
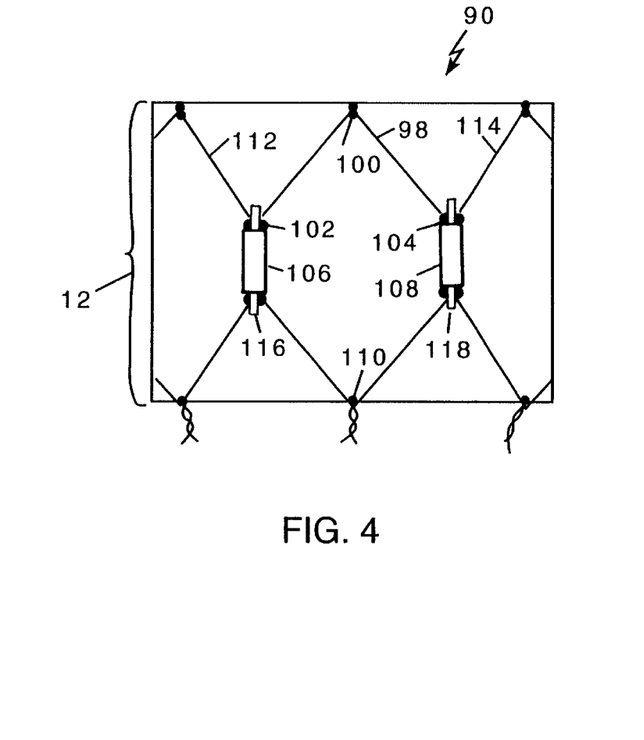
FIGS. 4–4A are diagrammatic side views of a filter and forming mandrels at different stages in a process for fabricating the filter shown in FIGS. 1–1b and 2–2B.
Figure 4A:
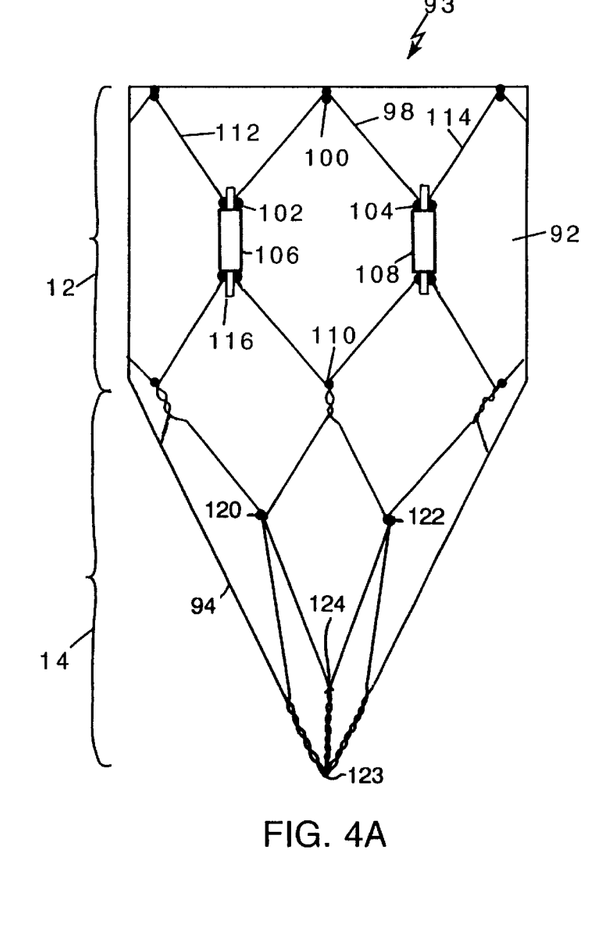

Referring to FIGS. 4 and 4A, in a process for fabricating a filter 10, a cylindrical thermally conductive mandrel 90 (e.g., formed from copper) is sized and constructed to conform to the desired filter size and shape. Mandrel 90 includes a plurality of anchoring pins protruding from its outer surface in a pattern corresponding to the desired cellular pattern for the filter.

As shown in FIG. 4, the process for fabricating the anchoring portion of the filter includes the following steps. A wire strand 98 is bent around an anchoring pin 100 to form the proximal end of anchoring portion 12 of the filter. The two ends of wire strand 98 are pulled divergently downward to pins 102, 104 and through respective hypotubes 106 and 108. The strands are bent convergently further downward to pin 110 (located about 23 mm distally from anchoring pin 100), below which they are helically twisted about each other through two turns. The same steps are performed for neighboring strands 112 and 114. Hooks 116, 118 are also passed through hypotubes 106, 108. The respective hypotube assemblies are joined by resistance welding under an inert gas shield using about 70 ounces of force and about 10 Joules of heat.

As shown in FIG. 4A, the process for fabricating the filtering portion includes the following steps. The previously formed anchoring portion 12 of the filter is positioned about a cylindrical portion 92 of a mandrel 93 (e.g., formed from aluminum or stainless steel), which includes a conical portion 94. The ends of strand 98 are pulled divergently downward to pins 120, 122 (located about 22 mm proximally from the distal end 123 of mandrel 91), below which the strands are helically twisted through two turns with respective ends of neighboring strands 112, 114. The ends of strand 98 are convergently pulled further downward to pin 124 (located about 8 mm proximally from the distal end 123 of mandrel 91), below which the ends of strand 98 are helically twisted about each other through about 4–7 turns to the apical distal end of the filtering portion. The resulting six pairs of helically twisted strands are passed through a short hypotube (not shown), the top of which is TIG welded to securely fix all of the strands.

A metallic wire is wrapped about the filter/mandrel assembly to tightly secure the relative positions of the elongated wire strands defining the cells in the anchoring and filtering portions. The filter and the forming mandrel are then placed in an oven set to a temperature of about 450° C. for a period of 15 to 20 minutes. Prior to this heat treatment the nitinol wires are relatively malleable, but after heat treatment the nitinol wires strands preferentially maintain their shape. Once the mandrel has cooled the anchoring pins are removed and the filter is removed from the mandrel.

Figure 5:
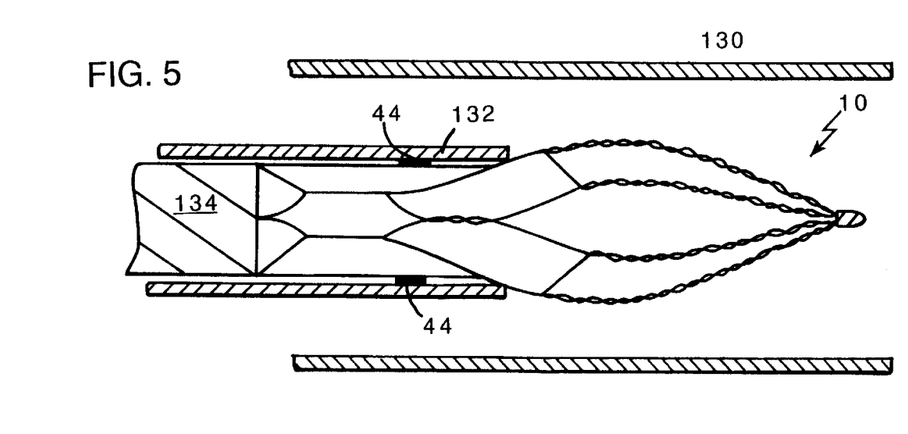
FIG. 5 is a diagrammatic side view of a filter being delivered to a blood vessel.
Figure 5A:
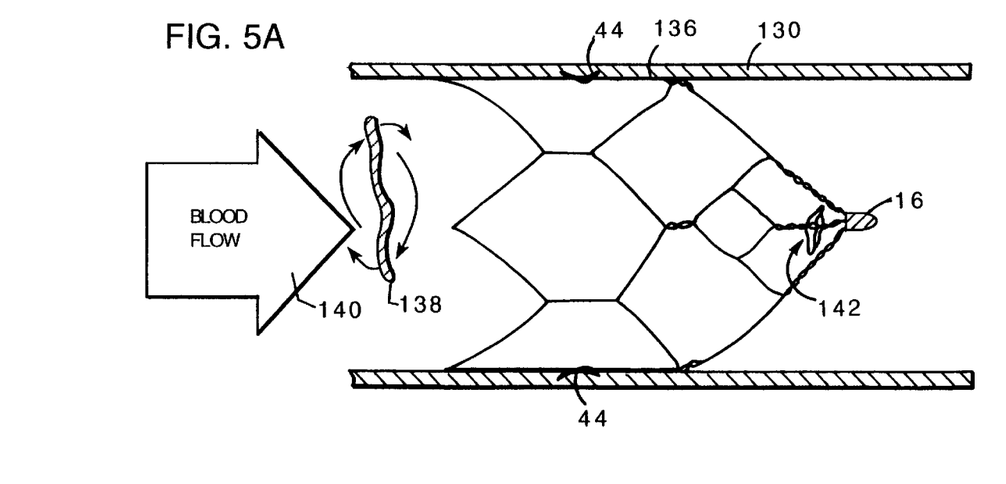
FIG. 5A is a diagrammatic side view of a filter anchored in a blood vessel.

Referring to FIGS. 5 and 5A, a blood clot filter 10 is delivered to a desired location within a vessel 130 (e.g., a vena cava having a diameter on the order of about 20 mm) through a previously inserted teflon sheath 132. Sheath 132 having an outer diameter on the order of about 3 mm is inserted percutaneously, e.g., via a small opening (on the order of 9 Fr (about 0.117 inch)) in the groin and into the femoral vein of a patient. A pusher 134, extending proximally to a location outside of the patient, is used to advance filter 10 through the sheath. Once the distal end of the sheath is properly positioned in vessel 130, pusher 134 advances filter 10 to the distal end of the sheath and holds filter 10 in the desired position in the vessel. The sheath is then pulled back, releasing the filter within vessel 130, as shown in FIG. 5A. Once the filter is released, the sheath and the pusher can be withdrawn from the patient as a single unit.

Referring to FIG. 5A, after the filter is released within vessel 130, the self-expanding cells of the anchoring portion urge the anchoring portion to outwardly expand against an inner wall surface 136 of vessel 130 with sufficient force to prevent migration of the filter through the vessel. Within sheath 132 hooks 44 lie flat and conform to the shape of the cylindrical portion to allow the filter to slide through the sheath, but when the filter is released from the sheath the hooks spring outwardly from the anchoring portion of the filter for engagement with wall surface 136. The expansion of the anchoring portion imbeds hooks 44 into the walls of the vessel to further secure the filter within the vessel.

We note that FIGS. 5 and 5A are not drawn to scale, but instead are drawn diagrammatically for purposes of illustration.

In operation, the filter captures a blood clot 138 in blood flow 140 (e.g., on the order of 1 liter per minute) by guiding the clot to the apical distal end 16 of the filtering portion. Captured clots 142 are maintained in the central region of the blood flow where the velocity is highest to achieve the most effective lysing action.

As mentioned above, the sizes of the cells in the filtering portion are selected to be small enough to capture clots of a specified size with a desired level of efficiency (e.g., with clot capturing efficiency and patency comparable to a GREENFIELD® 24 Fr stainless steel filter, available from Medi-Tech, Inc. of Watertown, Mass., U.S.A.). Thus, it is desirable to reduce the size of the cells to increase the efficiency of clot capture. However, smaller cells create greater turbulence in the blood flow, encouraging clot formation on the filter that may result in the occlusion of a vessel. A filter according to the invention minimally disturbs blood flow, while achieving a desirable level of filtering efficiency. The sizes of the cells in the filtering portion decrease the closer they are to the apical distal end 16. Thus, cell size in the filtering portion varies inversely with blood flow velocity: larger cells are positioned near the vessel walls where the flow velocity is relatively low and smaller cells are positioned in the central region of the vessel where the flow velocity is highest. Clots traveling with lower velocity do not pass through the larger size cells in the periphery of the conical filtering portion, but are instead guided to the apical distal end of the filtering portion. Clots traveling with higher velocities in the central region of the vessel, which may otherwise pass through the larger size peripheral cells, are caught in the smaller size cells located at the distal end of the filtering portion.

Other Embodiments

Figure 6:
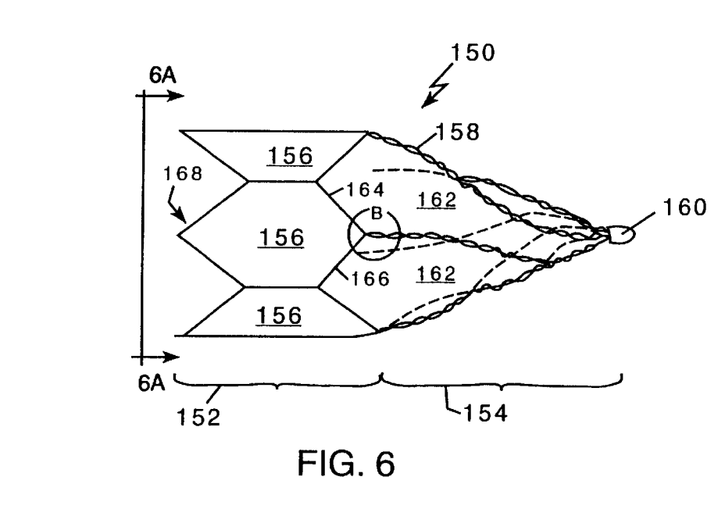
FIGS. 6 and 6A are diagrammatic side and end views of a filter.
Figure 6A:
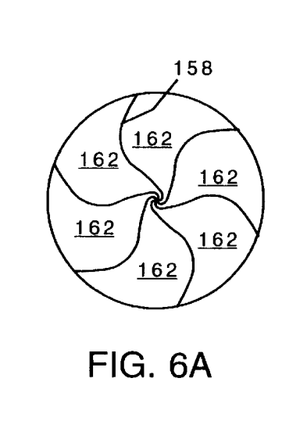
Figure 6B:
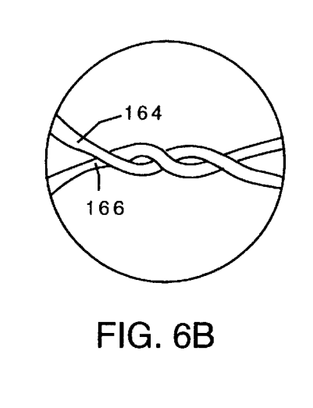
FIG. 6B is an enlarged view of a portion of the filter shown in FIG. 6.

Referring to FIGS. 6–6B, a blood clot filter 150 includes a generally cylindrical anchoring portion 152 and a generally conical filtering portion 154. Anchoring portion 152 includes a ring of cells 156 and is constructed in a similar manner as anchoring portion 12 of filter 10, shown in FIGS. 1–1C and 2–2B. Filtering portion 154 is formed from six spirally arranged legs 158 terminating at an apical distal end 160.

Legs 158 of the filtering portion of the filter are twisted through 900 over a length of about 32–34 mm. Twisting legs 158 creates a series of spirally arranged cells 162. The projection of legs 158 in a plane transverse to the longitudinal axis of the anchoring portion reveals that the cells defined by legs 158 decrease in size from the peripheral edge of the filtering portion to the apical center; the amount of reduction being determined by the twist pitch (degrees of rotation per unit length) and the number of legs 158 in the filtering portion. This reduction in cell size achieves an advantage similar to the advantage achieved by the reduction in cell size in the embodiment of FIGS. 1–1C and 2–2B, as described above.

As shown in FIG. 6B, legs 158 are formed from pairs of elongated strands of resilient material (e.g., nitinol wire) 164, 166 helically twisted about each other. Strands 164, 166 correspond to the respective ends of strands 168 that are bent into a V-shape to form the proximal end of anchoring portion 152. Twisting strands 164, 166 increases the rigidity of legs 158 for maintaining the structural integrity of the generally conical filtering portion. Increasing the rigidity of legs 158 also prevents clots from forcing their way past the filter by displacing the relative positions of the legs.

Figure 7:
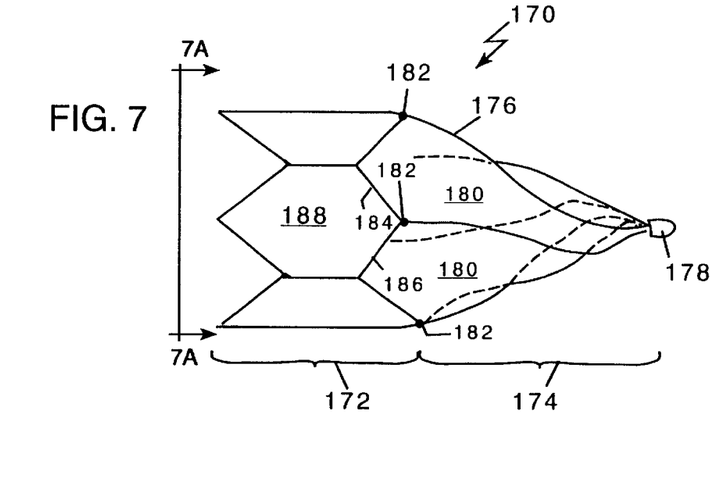
FIGS. 7 and 7A are diagrammatic side and end views of a filter.
Figure 7A:
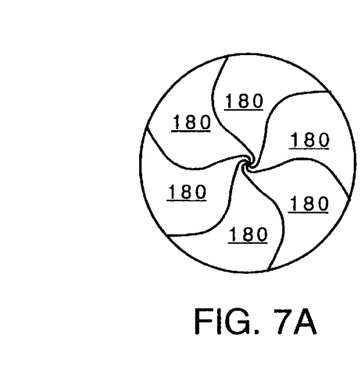

Referring to FIGS. 7–7A, in another filter embodiment 170, a generally cylindrical anchoring portion 172 is constructed in a similar manner as anchoring portion 12 of filter 10, shown in FIGS. 1–1c and 2–2B. A generally conical filtering portion 174 is formed from six spirally arranged legs 176 terminating at an apical distal end 178.

Legs 176 of filtering portion 174 are twisted through 900 over a length of about 32–34 mm, as in the filter embodiment shown in FIGS. 6–6B, creating a ring of spirally arranged cells 180. However, each leg 176 is formed from the continuation of a single elongated strand (formed from, e.g., nitinol wire) from the anchoring portion. To increase the structural integrity of the anchoring portion and the filtering portion, a series of spot welds 182 are provided at the distal end of the anchoring portion, joining strands 184, 186 that define cell 188.

Figure 8:
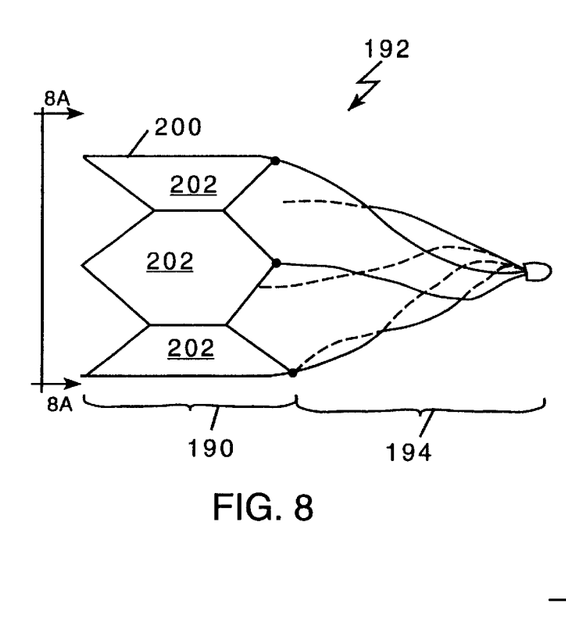
FIG. 8 is a diagrammatic side view of a filter.
Figure 8A:
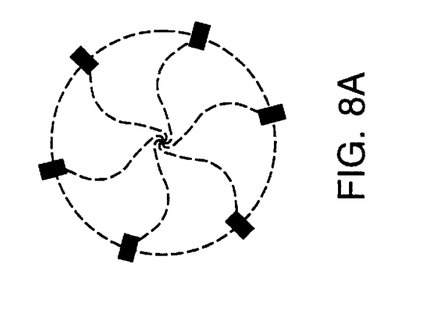
FIGS. 8A and 8B are diagrammatic end views of the filter of FIG. 8 in an expanded condition and in a compressed condition, respectively.
Figure 8B:
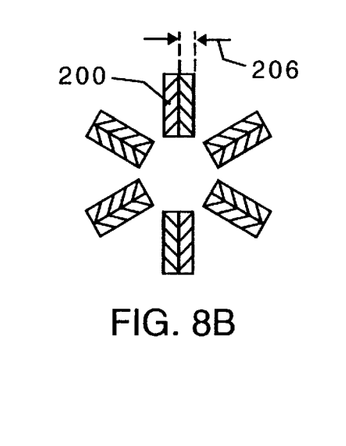

As shown in FIGS. 8–8B, the anchoring portion 190 of a filter 192 may be formed from flat strands 200 (e.g., formed from superelastic material such as nitinol wire) having a rectangular cross-section. The anchoring portion of the filter is shown in an expanded condition in FIG. 8 and in a compressed condition in FIG. 8A. The flat strands are arranged in the form of a ring of cells 202 (e.g., six cells), with the number and size of the cells being selected to provide a desired level of anchoring force. The width dimension 204 (on the order of 0.5–0.7 mm wide) of flat strands 200 is oriented radially and the thickness dimension 206 (on the order of 0.05–0.15 mm thick) is oriented circumferentially. This strand orientation provides a high radial force-to-compressed profile ratio. Also, use of flat strands facilitates manufacture of the filter because there is more strand material available for welding. A filtering portion 194 (e.g., a conical filtering portion) may be formed from spirally arranged wires as shown or may be formed from rings of cells, as in the filter of FIG. 1. The filtering portion may be formed from the extension of flat strands 200. Alternatively, a filtering portion may be formed from round wire that may be joined to the flat strand anchoring portion by welding with a hypotube arranged as a universal-type hinge, or by using an adhesive or sutures.

Although the invention has been described in connection with blood clot filtering in the vena cava, the present invention would also be useful for filtering clots in other areas of the vascular anatomy. For example, blood clot filtering may be useful in vessels leading to the brain. The filter used in such applications would be constructed of appropriate size and of appropriate material to provide proper anchoring force against an inner wall surface of the vessel in which the filter is disposed.

In further embodiments, the respective strands 38 and hooks 44 in regions of contact 40 (FIG. 1) in the anchoring portion of the filter may be joined together using laser welding along a length of about, e.g., 2–3 mm, instead of using a hypotube and resistance welding.

In other embodiments, the filter may be of the non-self-expanding type, preferably delivered using a catheter having an expandable balloon. The cells can be made of plastically deformable material, which may be, for example, tantalum, titanium, or stainless steel.

In still other embodiments, the filter may be formed of a temperature-sensitive shape memory material with a transition temperature around body temperature. The filter may then be delivered in a compressed condition in one crystalline state and expanded by crystalline phase transformation when exposed to body temperature.

In other embodiments, at least a portion of the filter may be formed from nitinol wire having a core of tantalum wire or other radiopaque material, as described in U.S. Ser. No. 07/861,253, filed Mar. 31, 1992 and U.S. Ser. No. 07/910,631, filed Jul. 8, 1992, both of which are herein incorporated by reference. This enhances the radiopacity of the filter so that the filter may be viewed using X-ray fluoroscopy to monitor placement and operation of the filter.

In still other embodiments, the filter may be coated with a drug for in vivo compatibility prior to delivery into the body. For example, the filter may be coated with heparin, as described in U.S. Pat. Nos. 5,135,516 and 5,304,121, which are herein incorporated by reference.

Other embodiments are within the scope of the claims.

What is claimed is:

1. An anchoring apparatus for anchoring a cylindrical portion of an implantable blood clot filter device to a wall of a body vessel, comprising:

a tubular member attachable to said cylindrical portion of said device; and an elongated member discrete and separate from said implantable device and adapted to be supported thereby, wherein the elongated member further terminates in ends extending from corresponding ends of the tubular member for engaging the wall of the vessel.

2. The anchoring apparatus of claim 1, wherein the ends of the elongated member extend in opposing directions.

3. The anchoring apparatus of claim 1, wherein each end of the elongated member includes a bend.

4. The anchoring apparatus of claim 1, wherein the elongated member comprises:

a first portion extending from an end of the tubular member and diverging from a longitudinal axis of the tubular member; and a second portion extending from another end of the of the tubular member and diverging from the longitudinal axis.

5. The anchoring apparatus of claim 1, wherein the elongated member comprises a compliant material.

6. The anchoring apparatus of claim 1, wherein the elongated member comprises nitinol.

7. The anchoring apparatus of claim 1, wherein the elongated member comprises a wire.

8. The anchoring apparatus of claim 7, wherein the wire includes a substantially flat surface.

9. The anchoring apparatus of claim 7, wherein the wire comprises pointed ends for piercing the wall of the vessel.

10. The anchoring apparatus of claim 9, wherein the wire comprises a flat wire formed of compliant material, and includes a bend on each side of the tubular member.

11. The anchoring apparatus of claim 1, wherein the elongated member has a length of about 5 mm, width of about 0.5 mm, and a thickness in a range of about 0.05 to about 0.15 mm.

12. The anchoring apparatus of claim 1, wherein the tubular member comprises a cylindrical tube.

13. An implantable blood clot filter device for implantation in a body vessel having a wall, comprising:

an anchoring apparatus, including a tubular member, and a wire member extending through the tubular member and having an end portion extending out from an end of the tubular member for engaging the wall of vessel; and a blood clot filter including an elongated strand for positioning in adjacent contact with said vessel wall and extending through the tubular member, said wire being descrete and separated from said elongated strand of said blood clot filter, wherein both the wire and the tubular member are fixed relative to the elongated strand.

14. The implantable device of claim 13, wherein the end portion comprises a bend.

15. The implantable device of claim 13, wherein the wire further includes a second end portion extending from another end of the tubular member.

16. The implantable device of claim 15, wherein the end portions of the wire extend in opposing directions relative to a longitudinal axis of the tubular member.

17. The implantable device of claim 15, wherein each wire end portion comprises a bend.

18. The implantable device of claim 13, wherein the end portion of the wire diverges from a longitudinal axis of the tubular member, and wherein the wire further comprises a second end portion extending from another end of the tubular member and diverging from the longitudinal axis.

19. The implantable device of claim 13, wherein the wire is formed of a compliant material.

20. The implantable device of claim 13, wherein the wire includes a substantially flat side.

21. The implantable device of claim 13, wherein the tubular member is cylindrical.

22. The implantable device of claim 13, wherein the device is formed by a process comprising:
   extending the strand through the tubular member;
   extending the elongated member through the tubular member; and
   fixing the tubular member and the elongated member relative to the strand.

23. An implantable blood clot filter device comprising a generally cylindrical portion including an elongated strand attached to an anchoring means for anchoring the cylindrical portion to a wall of the vessel, wherein the anchoring means includes a tubular member oriented along a longitudinal axis and surrounding the elongated strand for positioning adjacent said vessel wall, and an elongated member extending through the tubular member, the elongated member being formed of a compliant material, having a substantially flat side, and having first and second end portions extending from corresponding ends of the tubular member for engaging the wall of the vessel, the first and second end portions of the elongated member diverging from the longitudinal axis, and wherein both the elongated member and the tubular member are fixed relative to the elongated strand.

24. An anchorable implantable device for anchoring within a blood vessel comprising:
   a blood clot filter including a generally cylindrical section and a conical section axially aligned with said generally cylindrical section, and
   an anchoring apparatus projecting from said blood clot filter so as to engage a wall of a blood vessel and anchor said blood clot filter within said blood vessel, wherein said anchoring apparatus includes a tubular member attached to said cylindrical section for positioning adjacent said vessel wall and an elongated member supported by and extending through said tubular member.

25. An anchorable implantable device as in claim 24, wherein said elongated member further comprises ends extending from corresponding ends of said tubular member for engaging the wall of the blood vessel.

26. An anchorable implantable device as in claim 25, wherein said ends of said elongated member extend in opposing directions.

27. An anchorable implantable device as in claim 25, wherein each of said ends of said elongated member includes a bend.

28. An anchorable implantable device as in claim 24, wherein said elongated member comprises:
   a first portion extending from an end of said tubular member and diverging from a longitudinal axis of the tubular member; and
   a second portion extending from another end of said tubular member and diverging from a longitudinal axis of the tubular member.

29. An anchorable implantable device as in claim 24, wherein said filter includes a plurality of closed cells.

30. An anchorable implantable device as in claim 24, wherein said conical section includes a plurality of closed cells.

31. A blood clot filter as in claim 30, wherein said plurality of closed cells of said conical section form a series of circumferential rings.

32. An anchorable implantable device as in claim 31, wherein said series of circumferential rings of said conical section decrease in circumference along an axis of said conical section.

33. An anchorable implantable device as in claim 24, wherein said generally cylindrical section includes a plurality of closed cells forming a series of circumferential rings.

34. An anchorable implantable device as in claim 24, wherein said conical section includes a series of elongated strands tapering to form said conical section.

35. An anchorable implantable device as in claim 24, wherein said conical section is tapered toward a distal apical tip.

36. An anchorable inplantable device as in claim 24, wherein said filter is formed from material selected from the group consisting of polymeric material, plastically deformable material, metallic material and shape-memory material.

37. A blood clot filter as in claim 36, wherein said shape memory material is nitinol.

38. A blood clot filter as in claim 24, wherein said generally cylindrical portion is expandable from a low-profile compressed condition to a larger profile expanded condition.

39. A blood clot filter as in claim 38, wherein said generally cylindrical portion is self-expandable.

40. A blood clot filter as in claim 24, further comprising one or more hooks mounted on said generally cylindrical section.

41. A blood clot filter as in claim 40, wherein said hooks are fixedly coupled to said generally cylindrical portion.

* * * * *

UNITED STATES PATENT AND TRADEMARK OFFICE
CERTIFICATE OF CORRECTION

PATENT NO.    : 6,273,900 B1                                Page 1 of 1
DATED         : August 14, 2001
INVENTOR(S)   : Nott et al.

It is certified that error appears in the above-identified patent and that said Letters Patent is hereby corrected as shown below:

<u>Title page,</u>
Item [75], Inventors, reads "...Naroun Soun...", and should read -- ...Naroun Suon... --.

Signed and Sealed this

Eighteenth Day of March, 2003

JAMES E. ROGAN
*Director of the United States Patent and Trademark Office*